United States Patent [19]
Takahashi et al.

[11] Patent Number: 4,628,092
[45] Date of Patent: Dec. 9, 1986

[54] TRIETHYLENEDIAMINE CONTAINING ACETYLENIC ALCOHOLS AS FLOW AIDS

[75] Inventors: Akio Takahashi, Macungie; Robert G. Petrella, Allentown, both of Pa.

[73] Assignee: Air Products and Chemicals, Inc., Allentown, Pa.

[21] Appl. No.: 747,620

[22] Filed: Jun. 21, 1985

[51] Int. Cl.[4] .................... C07D 487/08; B01J 2/30
[52] U.S. Cl. .................................... 544/351; 252/384
[58] Field of Search .......................... 544/351; 252/384

[56] References Cited

U.S. PATENT DOCUMENTS

| 3,240,558 | 3/1966 | Heiss | 252/384 |
| 3,457,304 | 7/1969 | Amstutz | 252/384 |
| 3,925,226 | 12/1975 | Takenouchi | 252/384 |
| 4,345,079 | 8/1982 | Hyman et al. | 544/351 |
| 4,559,384 | 12/1985 | Nomura | 252/384 |

FOREIGN PATENT DOCUMENTS 62315 6/1968 German Democratic Rep. .
203039 12/1982 Japan .

Primary Examiner—Mark L. Berch
Attorney, Agent, or Firm—Michael Leach; James C. Simmons; E. Eugene Innis

[57] ABSTRACT

The flowability of stored triethylenediamine is improved by admixing with a flow promoting amount of a $C_5$–$C_{28}$ acetylenic alcohol. Especially suitable as a flow promoting additive for triethylenediamine is a mixture of 3,6-dimethyl-1-heptyne-3-ol and 3,5,8,10-tetramethyl-6-dodecyn-5,8-diol.

16 Claims, No Drawings

TRIETHYLENEDIAMINE CONTAINING ACETYLENIC ALCOHOLS AS FLOW AIDS

TECHNICAL FIELD

The invention relates to triethylenediamine crystal and, more particularly, relates to powdery triethylenediamine containing flow control additives.

BACKGROUND OF THE INVENTION

Triethylenediamine (TEDA), also known as 1,4-diazabicyclo(2.2.2) octane, is well known in the commercial market as a catalyst or cocatalyst in the production of polyurethane plastics, elastomers and foams. A number of methods are known in the art for preparing and isolating this compound as a product of commercially acceptable purity.

The production of TEDA may employ as a starting material an alkylene polyamine, mono- or bis-hydroxyethyl piperazine, N-aminoethyl piperazine, or alkanolamines alone or in mixture with ethylenediamine.

Typically, the TEDA is isolated from the reaction mixture as a white crystalline hygroscopic product containing a small amount of by-product amine compounds. The TEDA product is generally placed on the market for commercial users in drums of about 25 kg capacity.

With improved purification the synthesized TEDA product is recovered having less than about 500 ppm by-product organic amine impurities. It was found, however, that the purified commercial powdery crystalline TEDA product of this desired low content of organic amine impurities, when stored in commercial size drums for even short periods, particularly in a moderately warm environment, tended to develop a caking, or blocking, problem. This bulk aggregation of the powdery crystals is believed the result of two factors, namely (a) sublimation and recrystallization of the TEDA molecules forming a bridge between adjacent particles and (b) hygroscopicity which also results in agglomeration of adjacent particles. Thus the stored powdery product becomes very difficult to remove from the drum by pouring or scooping.

Japanese Patent Publication No. 82-203039 of Toya Soda Kogyo Co., Ltd. discloses non-solidifying triethylenediamine compositions comprising 0.01-2 parts by weight silica per 100 parts by weight triethylenediamine crystals. The bulk density of the silica should be less than 200 g/l. The insolubility of colloidal silica can cause problems with the use of such treated TEDA in aqueous and non-aqueous catalyst solutions.

U.S. Pat. No. 4,345,079 discloses a scoopable triethylenediamine containing a minor amount of an additive in liquid form which is a polyethylene glycol, a glycol ester, a glycol ether or an amino alcohol. Carbowax 400 polyethylene glycol was the preferred additive.

SUMMARY OF THE INVENTION

According to the present invention the flowability of triethylenediamine can be improved when a flow promoting amount of certain additives are admixed with the TEDA powder. The materials which are flow improving additives according to the invention are $C_5$-$C_{28}$ acetylenic alcohols.

TEDA compositions containing additives according to the invention remain as a flowable powder for a longer period and are much easier to render free flowing than TEDA product compositions according to the prior art.

DETAILED DESCRIPTION OF THE INVENTION

As flow promoting additives, the acetylenic alcohols may be admixed with the TEDA powder in any manner effective to obtain good dispersion throughout the mass. The admixing may be performed at a temperature ranging from ambient up to the melting point of the TEDA powder. The preferred additives are those which do not adversely affect the appearance or performance of the TEDA or blends of TEDA, such as aqueous solutions or mixtures with dipropylene glycol or dimethylethanolamine in catalyzed urethane and isocyanurate formation. A flow promoting amount of the acetylenic alcohols is mixed with the TEDA powder, such as 0.01-1 parts of the acetylenic alcohol per 100 parts of TEDA. While a degree of improvement in flowability is obtained when about 0.01% of the additive is used, such lower levels have not been found to afford the desired flowability of the TEDA for sufficiently long storage periods at warmer temperatures at greater than 1 part/100 parts TEDA no additional advantage is obtained.

The acetylenic alcohols are relatively water insoluble in that they are typically only soluble in water at less than about 2 grams per 100 grams of water. This does not, however, present a problem when the TEDA is employed in formulations in which it is dissolved in water, for example in the production of water-blown flexible polyurethane foams because the actual use level is so low water solubility will usually be achieved. Water-solubility is not required where the TEDA is used as a catalyst in non-aqueous urethane formulations, isocyanate polymerization or the like provided that the additive is sufficiently soluble in the polyol or other organic solvent or component of the formulations with which TEDA is to be mixed.

The TEDA flow promoting additives according to the invention are $C_5$-$C_{28}$ acetylenic alcohols which is meant to include acetylenic diols. Suitable acetylenic alcohols and diols may be represented by the following general formulas

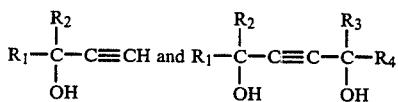

where $R_1$ and $R_4$ are $C_1$-$C_{10}$, preferably $C_1$-$C_5$, alkyl groups, which may be branched or unbranched, such as ethyl, n-propyl, isopropyl, isobutyl, 2-methylpentyl and the like; and $R_2$ and $R_3$ are methyl or ethyl.

Examples of such flow promoting aids include 2-methyl-1-butyne-2-ol; 3,6-dimethyl-1-heptyne-3-ol; 3,6-dimethyl-4-octyne-3,6-diol; 2,4,7,9-tetramethyl-5-decyne-4,7-diol; and 3,5,8,10-tetramethyl-6-dodecyne-5-8-diol. The acetylenic alcohols may be used individually or in mixtures with each other, for example ranging from 1:10 to 10:1 on a weight basis.

Such acetylenic alcohols and diols can be prepared according to the teachings of U.S. Pat. Nos. 3,082,260, 3,462,499 and 3,709,946. Certain acetylenic alcohols are commercially available from Air Products and Chemicals, Inc. under the registered trademark "Surfynol".

In the following examples the flowability of TEDA was tested and rated as follows:

TEDA containing the indicated amount of a flow promoting additive was mixed in a Hobart mixer at speed #1 (139 gyrations/min.) at the specified heating mantle temperature for the specified time.

One pound of treated TEDA was placed in a 1 quart glass jar with a large mouth, capped tightly with a plastic cap and maintained at a selected temperature. Periodically, the jar was uncapped and a screwdriver with a shaft of ¼"×¼" thickness and 8" length was manually driven through the TEDA in the jar. The flowability was rated by the magnitude of the force required to get the screwdriver through the TEDA mass as follows:

Poor—The screwdriver could not get through to the bottom of the jar. The entire TEDA mass was caked and difficult to break up into a powder.

Good—The screwdriver got through to the bottom of the jar. The TEDA mass was caked but could be broken up to a lump and then to a powder with some effort.

Excellent—The screwdriver got through with very little force. The entire TEDA mass broke into free flowing powder.

EXAMPLE 1

Various additives were subjected to a prescreening test to determine their suitability for improving flowability of plant produced TEDA having a content of by-product amine impurities in the range of about 100–500 ppm. The designated additives were incorporated in the respective amounts set forth in Table I with 900 g of TEDA. After mixing at the indicated temperature for 0.5 hours the product mixture was stored in two jars, one kept at room temperature for 16 hours and the other at 120° F. (49° C.) for one week.

hours at room temperature and one week at 120° F. The Toya Soda TEDA product which is believed to contain silica as a flow aid (Run 2) showed very good flowability after the 16 hour/room temperature storage but showed poor flowability after one week at 120° F. Run 4 which used a colloidal silica additive gave similar performance.

Polypropylene glycol (Run 5) and polyethylene glycol (Run 6) present at a level of 4.5 grams per 900 grams TEDA showed fair and good flowability, respectively, at 16 hours/room temperature and were only rated fair and poor, respectively, at one week/120° F. The monomethyl ether of polyethylene glycol (Run 7), while rated good during the room temperature test, deteriorated to a fair rating over the longer test at higher temperature.

In contrast to the prior art additive-containing TEDA mixtures (Runs 3–7) which appeared to lose performance over the extended time period and elevated temperatures, the acetylenic alcohol-containing TEDA blends (Runs 8–16) demonstrated at least the same degree of flowability after one week at 120° F. as they did after 16 hours at room temperature. Only Run 9 using Surfynol 104 surfactant showed poorer flowability after storage for the extended period at elevated temperature; however, its flowability after 16 hr/RT storage was very good. The other acetylenic alcohols and mixtures thereof proved vastly superior as flow promoting additive for crystalline TEDA powder than the prior art. In fact, Run 16 which contained 0.5 wt % of a flow additive blend of 3,5,8,10-tetramethyl-6-dodecyne-5,8-diol and 3,6-dimethyl-1-heptyne-3-ol in a 75:25 weight ratio proved excellent under both storage conditions.

EXAMPLE 2

This Example presents flowability results comparing

TABLE I

| RUN | FLOW ADDITIVE (g) | TEDA (g) | MIXING TREATMENT (°F.) | FLOWABILITY 16 hr/RT | FLOWABILITY 1 wk./120° F. |
|---|---|---|---|---|---|
| 1 | | untreated | | poor | poor |
| 2 | | Toya Soda[j] | | very good | poor |
| 3 | Carbowax ® 400[a] (9) | 900 | RT | fair | poor |
| 4 | Hi Sil 233[b] (0.9) | 900 | RT | good | poor |
| 5 | Polypropylene Glycol[c] (4.5) | 900 | RT | fair | fair |
| 6 | Polyethylene Glycol[d] (4.5) | 900 | 250–300 | good | poor |
| 7 | Polyethylene Glycol Monomethyl Ether[e] (4.5) | 900 | 250–300 | good | fair |
| 8 | Surfynol 124[f] (4.5) | 900 | 250–300 | excellent | very good/excellent |
| 9 | Surfynol 104[g] (4.5) | 900 | 250–300 | very good | fair |
| 10 | Surfynol 72[h] (2.25) | 900 | RT | very good | very good |
| 11 | Surfynol 124 (2.25) | 900 | 250–300 | very good | very good |
| 12 | Surfynol 124 (0.9) | 900 | 250–300 | very good | very good |
| 13 | Surfynol 82[i] (2.25) | 900 | 250–300 | good | excellent |
| 14 | Surfynol 124/72 (75/25) (2.25) | 900 | RT | very good | excellent |
| 15 | Surfynol 124/72 (75/25) (0.9) | 900 | RT | very good/good | very good |
| 16 | Surfynol 124/72 (75/25) (4.5) | 900 | RT | excellent | excellent |

[a]Polyethylene glycol (400 molecular weight) marketed by Union Carbide
[b]A colloidal silica marketed by PPG Industries
[c]4,000 molecular weight
[d]18,000 molecular weight
[e]1,900 molecular weight
[f]3,5,8,10-tetramethyl-6-dodecyne-5,8-diol marketed by Air Products and Chemicals, Inc.
[g]2,4,7,9-tetramethyl-5-decyne-4,7-diol marketed by Air Products and Chemicals, Inc.
[h]3,6-dimethyl-1-heptyne-3-ol marketed by Air Products and Chemicals, Inc.
[i]3,6-dimethyl-4-octyne-3,6-diol marketed by Air Products and Chemicals, Inc.
[j]TEDA marketed by Toya Soda Kogyo Co., Ltd. believed to contain silica It can be seen from Table I that untreated TEDA powder (Run 1) demonstrated poor flowability after 16 acetylenic alcohol additives versus the polyethylene glycol and silica prior art additives. The indicated amount of additive was incorporated for 100 parts powdery TEDA crystal by mixing for 0.5 hr. at the indicated temperature in the Hobart mixer at 139 gyrations per minute. The flow additive treated TEDA was then tested for flowability at three different storage conditions. namely room temperature for 16-72 hours, 120° F. for 7 days and 120° F. for 14 days.

It can be seen from Table II that Runs 17-19 using the prior art treated TEDA blends all demonstrated significant deterioration in the flowability on exposure to elevated temperatures (120° F.) for extended periods (1 and 2 weeks). In marked contrast, the acetylenic alcohol treated TEDA blends all showed at least good flowability under the test storage conditions with the exception of the Surfynol 104 surfactant-containing composition which again had very good flowability after 16-72 hr/RT storage but only fair flowability after 7 days/120° F. The use of a mixture of Surfynol 124 and 72 surfactants as the flow promoting additive (Runs 25 and 26) afforded TEDA compositions which possessed excellent flowability under the three storage conditions.

TABLE II

| RUN | FLOW ADDITIVE[a] (pbw) | MIXING TREATMENT °F. | FLOWABILITY RT/16-72 HRS | 120° F./7 DAYS | 120° F./14 DAYS |
|---|---|---|---|---|---|
| 17 | CARBOWAX 400 (1.0) | RT | FAIR | POOR | POOR |
| 18 | TOYO SODA TEDA (—) | — | VERY GOOD | POOR | VERY POOR |
| 19 | HI SIL 233 (0.1) | RT | GOOD | POOR | — |
| 20 | SURFYNOL 124 (0.5) | 250-300 | EXCELLENT | EXCELLENT | EXCELLENT |
| 21 | SURFYNOL 124 (0.25) | 250-300 | VERY GOOD | VERY GOOD | VERY GOOD |
| 22 | SURFYNOL 104 (0.5) | 250-300 | VERY GOOD | FAIR | — |
| 23 | SURFYNOL 82 (0.25) | 250-300 | GOOD | GOOD (EXCELLENT WHEN IT IS STILL WARM) | |
| 24 | SURFYNOL 72 (0.25) | RT | VERY GOOD | GOOD/VERY GOOD | — |
| 25 | SURFYNOL 72/124[b] (25/75) (0.5) | RT | EXCELLENT | EXCELLENT | EXCELLENT |
| 26 | SURFYNOL 72/124 (60/40) (0.5) | RT | EXCELLENT | EXCELLENT | EXCELLENT |

[a]PART BY WEIGHT PER 100 PARTS TEDA
[b]25/75 Ratio of Surfynol 72/124 surfactants solidified on standing while 60/40 ratio stayed as a liquid.

STATEMENT OF INDUSTRIAL APPLICATION

The invention provides for improving the flowability of stored powdery TEDA crystals by the incorporation of a flow improving amount of an acetylenic alcohol.

We claim:

1. A method for improving the flowability of stored triethylenediamine which comprises mixing with the triethylenediamine a flow improving amount of a $C_5$–$C_{28}$ acetylenic alcohol.

2. The method of claim 1 in which the flow promoting additive is represented by either of the formulas

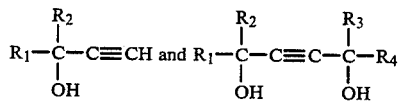

where $R_1$ and $R_4$ are $C_1$–$C_{10}$ alkyl groups, and $R_2$ and $R_3$ are methyl or ethyl.

3. The method of claim 1 in which 0.01–1 part of acetylenic alcohol is mixed per 100 parts triethylenediamine.

4. The method of claim 2 in which 0.01–1 part of the additive is mixed per 100 parts triethylenediamine.

5. The method of claim 4 in which the additive is 3,5,8,10-tetramethyl-6-dodecyne-5,8-diol.

6. The method of claim 4 in which the additive is 3,6-dimethyl-1-heptyne-3-ol.

7. The method of claim 4 in which the additive is 3,6-dimethyl-4-octyne-3,6-diol.

8. The method of claim 4 in which the additive comprises a mixture of 3,5,8,10-tetramethyl-6-dodecyne-5,8-diol and 3,6-dimethyl-1-heptyne-3-ol.

9. A composition consisting essentially of triethylenediamine admixed with a flow promoting amount of a $C_5$–$C_{28}$ acetylenic alcohol.

10. The composition of claim 9 in which the flow promoting additive is represented by either of the formulas $$R_1-\underset{\underset{OH}{|}}{\overset{\overset{R_2}{|}}{C}}-C\equiv CH \quad \text{and} \quad R_1-\underset{\underset{OH}{|}}{\overset{\overset{R_2}{|}}{C}}-C\equiv C-\underset{\underset{OH}{|}}{\overset{\overset{R_3}{|}}{C}}-R_4$$

where $R_1$ and $R_4$ are $C_1$–$C_{10}$ alkyl groups, and $R_2$ and $R_3$ are methyl or ethyl.

11. The composition of claim 9 in which 0.01–1 part of acetylenic alcohol is mixed with 100 parts triethylenediamine.

12. The composition of claim 10 in which 0.01–1 part of the additive is mixed per 100 parts triethylenediamine.

13. The composition of claim 11 in which the additive is 3,5,8,10-tetramethyl-6-dodecyne-5,8-diol.

14. The composition of claim 11 in which the additive is 3,6-dimethyl-1-heptyne-3-ol.

15. The composition of claim 11 in which the additive is 3,6-dimethyl-4-octyne-3,6-diol.

16. The composition of claim 11 in which the additive comprises a mixture of 3,5,8,10-tetramethyl-6-dodecyne-5,8-diol and 3,6-dimethyl-1-heptyne-3-ol.

* * * * *